(12) United States Patent
Semetey et al.

(10) Patent No.: US 10,098,984 B2
(45) Date of Patent: Oct. 16, 2018

(54) METHOD FOR GRAFTING POLYMERS ON METALLIC SUBSTRATES

(71) Applicants: INSTITUT CURIE, Paris (FR); CENTRE NATIONAL DE LA RECHERCHE SCIENTIFIQUE, Paris (FR); SORBONNE UNIVERSITÉ, Paris (FR)

(72) Inventors: Vincent Semetey, Le Mans (FR); Anne-Sophie Castanet, Le Mans (FR)

(73) Assignees: INSTITUT CURIE, Paris (FR); CENTRE NATIONAL DE LA RECHERCHE SCIENTIFIQUE, Paris (FR); SORBONNE UNIVERSITÉ, Paris (FR)

( * ) Notice: Subject to any disclaimer, the term of this patent is extended or adjusted under 35 U.S.C. 154(b) by 368 days.

(21) Appl. No.: 14/442,857

(22) PCT Filed: Nov. 19, 2013

(86) PCT No.: PCT/IB2013/060238
§ 371 (c)(1),
(2) Date: May 14, 2015

(87) PCT Pub. No.: WO2014/076682
PCT Pub. Date: May 22, 2014

(65) Prior Publication Data
US 2015/0283301 A1 Oct. 8, 2015

(30) Foreign Application Priority Data
Nov. 19, 2012 (EP) .................................... 12306440

(51) Int. Cl.
*A61L 27/34* (2006.01)
*B05D 5/08* (2006.01)
(Continued)

(52) U.S. Cl.
CPC ............. *A61L 27/34* (2013.01); *A61L 27/025* (2013.01); *A61L 27/06* (2013.01); *A61L 27/50* (2013.01);
(Continued)

(58) Field of Classification Search
CPC ....................................................... C07B 45/00
(Continued)

(56) References Cited

U.S. PATENT DOCUMENTS
2003/0104227 A1  6/2003  McCarthy et al.

FOREIGN PATENT DOCUMENTS
EP    1798250 A2   6/2007
WO   94/26321 A1  11/1994
(Continued)

OTHER PUBLICATIONS

Jan. 21, 2014 International Search Report issued in International Application No. PCT/IB2013/060238.
(Continued)

*Primary Examiner* — Dah-Wei D. Yuan
*Assistant Examiner* — Andrew J Bowman
(74) *Attorney, Agent, or Firm* — Oliff PLC (57) ABSTRACT

A method of conferring modified properties, e.g. modified physical and/or biochemical properties, to a metallic substrate surface, including at least two steps being (i) a first step including at least exposing the substrate surface to a hetero-bifunctional anchoring molecule carrying at least a silane group and at least a $A_1$ group, the $A_1$ group being optionally introduced within the anchoring molecule via a preliminary functionalizing step, and (ii) a second step of exposing the substrate surface to a polymer carrying at least three groups $A_2$ capable of reacting with $A_1$ in a thiol-ene
(Continued)

reaction, the number average molecular weight of the polymer being greater than 1 000 g/mol.

13 Claims, 2 Drawing Sheets

(51) Int. Cl.
*B05D 7/14* (2006.01)
*B05D 1/18* (2006.01)
*B05D 1/36* (2006.01)
*C07F 7/08* (2006.01)
*A61L 27/06* (2006.01)
*A61L 29/02* (2006.01)
*A61L 29/08* (2006.01)
*A61L 31/02* (2006.01)
*A61L 31/10* (2006.01)
*A61L 27/02* (2006.01)
*A61L 27/50* (2006.01)
*A61L 27/54* (2006.01)
*B05D 5/04* (2006.01)

(52) U.S. Cl.
CPC ............... *A61L 27/54* (2013.01); *A61L 29/02* (2013.01); *A61L 29/085* (2013.01); *A61L 31/022* (2013.01); *A61L 31/10* (2013.01); *B05D 1/185* (2013.01); *B05D 1/36* (2013.01); *B05D 5/08* (2013.01); *B05D 7/14* (2013.01); *C07F 7/0887* (2013.01); *A61L 2300/404* (2013.01); *A61L 2300/424* (2013.01); *A61L 2400/18* (2013.01); *A61L 2420/02* (2013.01); *B05D 5/04* (2013.01); *B05D 2202/35* (2013.01); *B05D 2203/30* (2013.01); *Y10T 428/31663* (2015.04)

(58) Field of Classification Search
USPC ........................................................ 427/2.1
See application file for complete search history.

(56) References Cited

FOREIGN PATENT DOCUMENTS

| WO | 97/27821 A1 | 8/1997 | |
|---|---|---|---|
| WO | 2005/084436 A1 | 9/2005 | |
| WO | 2012129380 A2 | 9/2012 | |
| WO | WO2012/129380 * | 9/2012 | ............. C07B 45/00 |

OTHER PUBLICATIONS

Jan. 21, 2014 Written Opinion issued in International Application No. PCT/IB2013/060238.

Roslyn Tedja et al., "Effect of TiO2 Nanoparticle Surface Functionalization on Protein Adsorption, Cellular Uptake and Cytotoxicity: The Attachement of PEG Comb Polymers Using Catalytic Chain Transfer and Thiol-ene Chemistry," Polymer Chemistry, vol. 3, No. 10, Jan. 1, 2012, p. 2743.

Alexander K. Tucker-Schwartz et al., "Thiol-ene Click Reaction as a General Route to Functional Trialkoxysilanes for Surface Coating Applications," Journal of the American Chemical Society, vol. 133, No. 29, Jul. 27, 2011, pp. 11026-11029.

Tosatti, S. et al., "Peptide Functionalized Poly(L-lysine)-g-poly(ethylene glycol) on titanium: resistance to protein adsorption in full heparinized human blood plasma", Journal of Materials Chemistry, Biomaterials vol. 24, 4949-4958, 2003.

Schliephake H. et al., "Chemical and biological functionalization of titanium for dental implants", Journal of Materials Chemistry, The Royal Society of Chemistry, J. Mater. Chem., vol. 18, 2404-2414, 2008.

Nanci, A. et al., "Chemical modification of titanium surfaces for covalent attachment of biological molecules", John Wiley & Sons, Inc., 324-335, 1998.

Perret, Emilie et al., "Versatile Decoration of Glass Surfaces to Probe Individual Protein-Protein Interactions and Cellular Adhesion", American Chemical Society, Langmuir, vol. 18, 846-854, 2002.

* cited by examiner

METHOD FOR GRAFTING POLYMERS ON METALLIC SUBSTRATES

The present invention relates to a method for covalently grafting polymers onto metal based substrates in order to confer modified physical properties thereto. The present invention relates more particularly to said method aimed at conferring to titanium-based substrates, the surface of which is formed at least partly by titanium oxide, anti-adhesive properties, cytotoxic properties such as antibiotic, bactericidal, viricidal and/or fungicidal properties, or properties promoting cell adhesion.

INTRODUCTION/PRIOR ART

Most metals and alloys used today in various applications present an at least partially passivated surface due to natural oxidation processes at ambient conditions and also due to adsorption of various molecules. For many applications, this passivated surface is an inherent advantage in terms of durability of the material, e.g. corrosion resistance.

For certain chemical and biomedical applications however, a custom-tailored functionalization of surface properties is highly desirable, e.g. for titanium-based materials, for example as medical implants, for surgical instruments, or for silicon-based materials, for example as biochips. In case of the latter, the control of different bioadhesive or biorepulsive properties, antibacterial, cell-promoting or other biocompatible characteristics is an important factor for a successful implant. Methods for modifying the surface of metal based substrates, notably when being formed at least partly by metal oxides, therefore are powerful tools for functionalising metallic materials.

Titanium for example is known to possess a very stable titanium oxide surface, which is why state of the art surface treatments of titanium-based substrates exhibit considerable drawbacks.

More particularly, titanium and titanium alloys are widely used in biomedical devices and components (medical device, dentistry . . . ). The material surface plays an extremely important role in the response of the biological environment to the artificial medical devices and in some applications, it is necessary to reduce surface protein adsorption and cell adhesion, for example in blood-contacting devices, such as stents, sensors, access port . . . that generates adverse biological reactions leading to complications like infections, occlusion, thrombosis, inflammation, fibrosis. No commercial solution is available to circumvent complications (infections, occlusions) associated with the use of titanium access ports in catheterism urging the need for strategies to lower complications.

PRIOR ART/DISADVANTAGES

Methods relying on simple adsorption, e.g. electrostatic interactions (S. Tosatti et al., *Biomaterials*, 24, pp. 4949-4958, 2003), for immobilising surface treatment molecules have a natural tendency for detachment of the immobilised molecules. Low stability of the immobilisation and non-defined release behaviour have been reported (see e.g. review by H. Schliephake and D. Schamweber, *J. Mater. Chem.*, 18, pp. 2404-2414, 2008).

Moreover, the article Tedja et al. (Pol. Chem., vol. 3, 10, p. 273) discloses a modification of titanium dioxide nanoparticles surfaces with polymeric chains by thiol-ene Michael nucleophilic addition. However, this addition involves a single reaction site on the modified polymer and the resulting link to the surface is susceptible of degradation. Indeed, ester functions (e.g. acrylate functions) are known for their instability which of course, in the present context of surface modifying processes is not an expected property.

One possible approach for a covalent immobilisation on titanium-based materials is to remove the passivating surface oxide layer so as to gain access to the more reactive, non-oxidised metallic part by using acidic etching solutions. This however necessitates the use of very aggressive chemicals such as a mixture of hydrofluoric acid, nitric acid and sulphuric acid (WO 97/27821) or other extensive cleaning procedures such as electrochemical polishing in a perchloric acid/butanol/methanol solution (WO 94/26321). These methods are mainly used to covalently attach biologically active molecules to the surface, either directly or via a linker group.

It has also been proposed to hydroxylate the surface oxide layer by treatment with strong oxidizing agents such as acids, hydrogen peroxide, oxide plasma or by calcining. In such a way, a direct covalent linkage of a low-molecular siloxane-based copolymer (2000 g/mol) to a thin titanium film has been shown (US 2003/0104227). Grafting of higher molecular weight polymers has not been demonstrated for this method and is not likely to lead to a high-density grafting of polymers. Application of this method is furthermore limited to a very specific class of hydrophobic siloxane polymers and notably excludes hydrophilic polymers, in particular those containing hydroxyl groups.

A very general and prospective divulgation (WO 2005/084436) indicates that polymers may be covalently bound to titanium dioxide particles seemingly without the need of a pre-treatment of the substrate. A trimethoxysilyl coupling agent bearing a methacrylate group is first attached on the particles and then copolymerised in situ on the surface with a quaternary amine containing diallyl monomer, initiated by an azo-compound. However, in situ copolymerisations need adjustments and techniques only available to trained specialists.

Although multi-step methods using aminosilanes have been used to immobilise biologically active molecules onto titanium-based surfaces (see A. Nanci et al., *J. Biomed. Mater. Res.*, 1998, 40, 324-335), no simple, efficient, versatile, reliable and industrially applicable method has been proposed so far for covalently attaching polymers onto metal-based substrates, notably when being formed at least partly by metal oxides, with a high polymer density and long-lasting durability of the immobilised polymer layer.

TECHNICAL PROBLEM

A need therefore exists for a simple, efficient and versatile method allowing a covalent immobilisation of polymers onto surfaces of metal-based substrates.

This need concerns especially methods which are not restricted to academic laboratory conditions but are industrially applicable.

A need also exists for a method allowing a covalent immobilisation of polymers onto metal-based substrates, notably when being formed at least partly by metal oxides, at high polymer surface densities.

It is moreover desirable to have at one's disposal a generic method able to confer to metal substrates a wide range of modified properties which can for example be chosen among: hydrophilic character; improved hydrophobic character, cytotoxic properties such as antibiotic, bactericidal, viricidal and/or fungicidal properties; cell-adhesion property; improved biocompatibility such as protein repellency or adhesion property; electric conductivity property and reactivity property which renders said surface able to immobilize biomolecules.

There exists furthermore a need for a functionalization method of metal substrates, which allows controlling said different properties.

There exists also a need for reducing surface protein adsorption and cell adhesion in biomedical devices and components comprising metallic surfaces in particular medical implants such as implantable catheters with access port.

SUMMARY OF INVENTION

Unexpectedly, the inventors have found that polymers carrying a thiol group, a disulphide or an alkenyl group can be easily reacted with a monolayer of molecules on a metal substrate surface with a free-standing alkenyl group or a thiol group, respectively, prepared by grafting a hetero-bifunctional anchoring molecule onto the metal substrate surface.

The thiol-ene reaction, not yet explored for grafting polymers onto surfaces, allows a simple, rapid, high-yielding and efficient immobilisation of the polymers by a photo-initiated reaction.

Therefore, the present invention proposes a method for covalently grafting polymers on metal-based substrates and more particularly on their surfaces being formed at least partly by metal oxides, such as surfaces of titanium-based materials.

The method comprises at least two steps, wherein the first of these two steps involves grafting a hetero-bifunctional anchoring molecule carrying at least a silane and at least a A1 group, said A1 group being optionally introduced within said anchoring molecule via a preliminary functionalizing step, said group A1 being capable of reacting in a thiol-ene reaction.

This first grafting generally leads to a very well organised, dense layer, commonly known as a self-assembled monolayer (SAM).

In a second step, the free-standing groups $A_1$ provide an attachment point for polymers containing a corresponding functional group $A_2$, and more preferably at least three functional $A_2$ groups, capable of reacting with the groups $A_1$ in a thiol-ene reaction.

According to the present invention, the group $A_2$ can also be called a reactive site.

The expression "reactive site" means a chemical function suitable to create covalent bonds with the hetero-bifunctional anchoring molecule carrying at least a silane group and at least a group $A_1$.

Thus, according to a first embodiment, the present invention concerns a method of conferring modified properties, e.g. modified physical and/or biochemical properties, to a metallic substrate surface, the surface being formed at least partly by metal oxides, comprising at least two steps consisting in:
  (i) a first step comprising at least exposing said substrate surface to a hetero-bifunctional anchoring molecule carrying at least a silane group silane and at least a A1 group, said A1 group being optionally introduced within said anchoring molecule via a preliminary functionalizing step, and
  (ii) a second step of exposing the substrate surface to a polymer carrying at least three groups $A_2$ capable of reacting with $A_1$, the second step being carried out after the first step, the group $A_1$ being an alkenyl group or —SH and the group $A_2$ being —SH or a group —S—S—R' when $A_1$ is an alkenyl group and $A_2$ being an alkenyl group when $A_1$ is —SH, with R' being a polymer, the number average molecular weight of said polymer being greater than 1 000 g/mol.

According to another embodiment, the present invention concerns a method of conferring modified properties, e.g. modified physical and/or biochemical properties, to a metallic substrate surface, the surface being formed at least partly by metal oxides, comprising at least two steps consisting in:
  (i) a first step comprising at least a) exposing said substrate surface to a hetero-bifunctional anchoring molecule carrying at least a silane group and b) functionalizing of the substrate surface with at least one group $A_1$, and
  (ii) a second step of exposing the substrate surface to a polymer carrying at least one group $A_2$ capable of reacting with $A_1$, the second step being carried out after the first step, the group $A_1$ being an alkenyl group or —SH and the group $A_2$ being —SH or a group —S—S—R' when $A_1$ is an alkenyl group and $A_2$ being an alkenyl group when $A_1$ is —SH, with R' being a polymer or an oligomer, the number average molecular weight of said polymer being greater than 1 000 g/mol.

According to another embodiment, the present invention concerns a method of conferring modified properties, e.g. modified physical and/or biochemical properties, to a metallic substrate surface, the surface being formed at least partly by metal oxides, comprising at least two steps consisting in:
  (i) a first step comprising at least exposing said substrate surface to a hetero-bifunctional anchoring molecule carrying at least a silane group and at least a $A_1$ group, said $A_1$ group being optionally introduced within said anchoring molecule via a preliminary functionalizing step, and
  (ii) a second step of exposing the substrate surface to a polymer carrying at least one group $A_2$ capable of reacting with $A_1$, the second step being carried out after the first step, the group $A_1$ being an alkenyl group and the group $A_2$ being —SH or a group —S—S—R' with R' being a polymer, the number average molecular weight of said polymer being greater than 1 000 g/mol.

It is furthermore known that molecules forming a SAM, presenting a certain degree of self-organisation, are packed/arranged very densely at the substrate surface. Since the thiol-ene type reaction is also very efficient and straightforward, the two-step grafting procedure according to the present invention enables the grafting of polymers at a high surface density, which is not possible by direct polymer grafting due to the sterical hindrance of large polymer molecules.

Among other advantages of the method according to the invention, the use of photo-initiators opens access to patterning of the immobilisation by applying appropriate photo-filters.

The surface density of the initial layer of molecules, in particular a SAM, being high and the thiol-ene reaction being high-yielding and efficient, the polymers can be grafted at a very high surface density onto the metal oxide surface.

The proposed two-step procedure allows a versatile functionalization, wherein the linker length, polymer characteristics, surface density and other important properties can be easily controlled and modulated.

According to one preferred aspect of the present invention, this method is used to confer anti-adhesive properties to titanium-based materials.

According to another embodiment, the present invention relates also to a metallic substrate, the surface of which has been treated by a method as described above.

According to yet another embodiment, the present invention relates also to a metallic substrate obtainable by a method as described above.

DEFINITIONS

For the purpose of this disclosure, the following definitions are provided.

Polymers

By "polymer" according to the present invention is meant a macromolecular compound comprising at least one type of covalently linked repeating units, called monomer units.

In the sense of the invention, molecules comprising 2 to 10 monomer units are "oligomers", whereas a "polymer" is a macromolecular compound comprising at least 11 monomer units.

The term "monomer" as used herein refers to a molecule or compound that usually contains carbon as its major component, is of relatively low molecular weight, and has a simple structure that is capable of assembling in polymeric chains by combination with itself or other similar molecules or compounds.

The term "monomer unit" as used herein refers to a constitutional unit of a polymer, which is formed starting from a unique monomer.

The polymer according to the present invention may be any kind of polymer and for example a homopolymer or a copolymer, wherein a homopolymer is a polymer comprising only one type of monomers and a copolymer is a polymer comprising two or more types of monomers, including furthermore polymers of all types of different architecture, such as a linear or a branched polymer, a block or statistical copolymer, star polymers and comb/brush polymers in the common sense known to a man skilled in the art.

Typically, a polymer in the sense of the invention presents a statistical distribution, concerning chain length, architecture, monomer types and molecular weight distribution.

If not otherwise indicated, the molecular weight of a polymer is understood to represent the number average molecular weight in the common sense known to a man skilled in the art.

Self-Assembled Monolayer (SAM)

In the sense of the present invention, the term "self-assembled monolayer" designates a layer formed by immobilisation of a molecule to the surface of a substrate, said layer being a monolayer, i.e. all molecules of the layer being attached to the surface, and said layer exhibiting at least partly a degree of self-organisation of architecture, e.g. alignments, due to attractive and/or repellent forces, e.g. hydrophilic/hydrophobic interactions, electrostatic interactions, hydrogen-bonding etc.

Hetero-Bifunctional Molecules

A molecule is "hetero-bifunctional" in the meaning of the present invention, if the molecule carries two distinct functional groups.

Thiol-Ene Reaction

The term "thiol-ene reaction" refers to a reaction between a first reactant comprising a thiol group or a disulphide group and a second reactant comprising an alkene moiety, leading to a covalent bond of first and second reactant by a thioether link.

The thiol-ene reaction may notably be photo-initiated.

Liquid Medium

The term "liquid medium" refers to a medium comprising an aqueous or organic solvent, a solvent being defined as any kind of substance liquid at ambient conditions, typically at a temperature of 25° C. and a pressure of 1 bar.

Advantageously, the liquid medium is able to dissolve at least partly the reactants of the step in which it is used, that is to say the anchoring molecule in the first step and the polymer carrying at least one group $A_2$ capable of reacting with the group $A_1$ in the second step.

Solvent

A solvent in the meaning of the invention is any kind of substance, liquid at ambient conditions, as mentioned above.

A solvent may for example be an organic solvent.

An organic solvent is e.g. a solvent chosen from the group consisting of alcohols, such as methanol and ethanol, esters such as ethyl acetate, ketones such as acetone, aliphatic solvents such as hexane, heptane, cyclohexane and mineral spirit, aromatic solvents such as toluene and benzene, aprotic solvents such as DMF, and halogenated solvents such as chloroform and dichloromethane.

Water may also be a solvent.

A solvent may also be an ionic solvent, such as methylimidazolium derivatives (1-Ethyl-3-methylimidazolium salts, 1-Propyl-3-methylimidazolium 1-Propyl-3-methylimidazolium, 1-Butyl-3-methylimidazolium salts . . . ).

Modified physical and/or biochemical property The term "modified physical and/or biochemical property" refers to any physical and/or biochemical property which is different from the original property of the surface to be treated. A surface which has been treated and which exhibits a "modified physical and/or biochemical property" extends to a surface bearing reactive groups able to react with a functional group on a biomolecule so biomolecules become covalently attached to the surface via the polymer.

Biocompatible

The term "biocompatible" as used herein refers to the capacity to be usable in biological environment in particular animal subjects, including humans. Biocompatibility may be achieved via various properties which are depending from the context of the application. For example, a material may be rendered biocompatible or may exhibit improved biocompatibility by improved protein repellency, by improved adhesion property or by introduction of any biological property which render the material compatible with its use in said biological environment, such as antithrombotic property.

Biomolecule

The term "biomolecule" as used herein encompasses any molecule known to be found in biological systems and includes amino acids, peptides, proteins, nucleic acids (including DNA and RNA), saccharides, polysaccharides, growth factors and glycoproteins. Biomolecule includes a biomolecule naturally occurring as well as a biomolecule which has been modified using techniques known from the man skilled in the art.

Efficient Conditions to

The term "efficient conditions to" means the usual conditions to perform a chemical reaction defined by the usual parameters, i.e. pH, temperature, solvent, duration, etc., which fall within the standard skills of a man of the art.

Able to Confer Said Modified Property

The term "able to confer said modified property" refers to the ability to confer said given property which can be measured at the macroscopic and/or microscopic scale by known methods.

Cytotoxic

For simplification reasons, in the framework of the invention, the term "cytotoxic", which is employed to qualify the modified properties of the substrate should be deemed to include not only the bactericidal or antibiotic properties, but also viricidal, fungicidal or in general any bioactive substance that is cytotoxic to any living cell the elimination of which is desired. Moreover, the term "anti-adhesive properties" encompasses the properties imparting repellency to proteins, bacteria, viruses, cells etc. . . .

Substituent Groups

The term "$(C_x-C_y)$alkyl" as used herein refers to a monovalent straight or branched-chain saturated hydrocarbon radical of x to y carbon atoms and their cyclic derivatives, unless otherwise indicated. Included within the scope of this term are such moieties as methyl, ethyl, isopropyl, n-butyl, t-butyl, t-butylmethyl, cyclopropyl, n-propyl, pentyl, cyclopentyl, n-hexyl, cyclohexyl, cyclohexylmethyl, 2-ethylbutyl, etc.

The term "$(C_x-C_y)$alkenyl" as used herein refers to a monovalent straight or branched-chain hydrocarbon radical of x to y carbon atoms comprising at least one insaturation, and their cyclic derivatives, unless otherwise indicated. Included within the scope of this term are such moieties as vinyl, allyl, isopropenyl, 1-propenyl, 1-butenyl, 2-butenyl, 3-butenyl, 1,3-butadienyl, etc.

The term "$(C_x-C_y)$aryl" as used herein refers to a monovalent aromatic hydrocarbon radical of x to y carbon atoms. Included within the scope of this term are such moieties as phenyl, biphenyl, naphthyl, indenyl and indanyl.

In the meaning of the invention, where the ending "-yl" is replaced by the ending "-ylene" in the above-mentioned terms, the term denotes the same radicals as mentioned before except that the radical is not mono-but bivalent.

The term "halogen" refers to a fluorine, chlorine, bromine or iodine atom. Bromine and chlorine are preferred halogen atoms in the framework of the present invention.

The term "$(C_x-C_y)$alkoxy" refers to a monovalent alkoxy radical made up of an oxygen radical bearing a saturated straight or branched chain hydrocarbon radical of x to y carbon atoms. Included within the scope of this term are methoxy, ethoxy, propoxy, n-butoxy, isobutoxy, sec-butoxy, t-butoxy, n-pentoxy, isopentoxy, sec-pentoxy, t-pentoxy and the like.

DETAILS OF THE INVENTION

In the following, the invention will be described in detail and by embodiments, being understood that certain specific embodiments are of explanatory nature and not intended to be limitative.

Substrate

A substrate in the meaning of the present invention is any metallic material including pure metals, metal alloys, metal oxide materials and mixtures thereof.

In the sense of the present invention, the metallic part of any compositions including metallic and non-metallic parts may be a substrate if the metallic part consists of a metallic material being a pure metal, a metal alloy, a metal oxide or a mixture thereof.

The surface of the substrate according to the present invention is characterized in that it comprises at least partly metal oxides, which may be hydroxylated under certain conditions e.g. in an aqueous environment.

Metallic material encompasses titanium, silicium, chromium, iron, nickel, aluminium, zirconium, tin, their alloys, their oxides and mixtures thereof.

Preferably, the substrate is a titanium-based material.

More preferably, the substrate surface comprises at least partly titanium oxide.

According to one specific embodiment, the substrate is titanium or a titanium alloy comprising a titanium oxide surface, and more preferably, said titanium or titanium alloy substrate is a medical implant comprising a titanium oxide surface.

According to another specific embodiment, the substrate is a silicon-based material comprising a silicium oxide surface, and more preferably, said silicon-based material is a biochip comprising a silicium oxide surface.

According to another specific embodiment, the substrate is an iron oxide-based material comprising an iron oxide surface, and more preferably, said iron oxide-based material is used in medical imaging techniques, in particular under the form of particles.

Method of Grafting

First Step: Covalent Attachment of Anchoring Molecules

The first step of the method of modifying a substrate surface according to the present invention involves exposing the substrate surface to anchoring molecules.

Anchoring Molecule

An anchoring molecule according to the present invention carries at least a silane group and enables the functionalization of the substrate surface with at least one group $A_1$ capable of reacting in a thiol-ene reaction.

The anchoring molecule may or may not carry the at least one group $A_1$. In the former case, the functionalization of the substrate surface with at least one group $A_1$ is achieved directly by exposing the substrate surface to the anchoring molecule. In other words, the anchoring molecule encompasses at least a silane group and at least a group $A_1$. In the latter case, said functionalization is achieved by modification and/or reaction of the layer, in particular a SAM, formed by exposing the substrate surface to the anchoring molecule. In other words, more than one reaction step is needed to obtain a modified surface comprising free $A_1$ groups.

According to one specific embodiment, the anchoring molecule is of the following formula (I):

wherein:

X represents a bivalent group chosen from the group consisting of a $(C_1-C_{18})$alkylene group optionally interrupted by 1 to 3 $(C_1-C_4)$alkenylene groups and/or 1 to 3 $(C_5-C_{10})$arylene groups and/or optionally substituted by 1 to 3 $(C_1-C_4)$alkenyl groups and/or 1 to 3 $(C_5-C_{10})$aryl groups, a bifunctional statistical polymer such as bivalent poly(1,2-butadiene) or bivalent polyisoprene for example having a molecular mass of 500 to 500 000 g/mol, preferably of 1000 to 50 000 g/mol, and more preferably of 2000 to 10000 g/mol and a 1,m-phenylene group with m=2, 3 or 4, R1, R2 and R3 represent independently a substituent chosen from the group consisting of a hydrogen atom, halogen atoms, $(C_1-C_6)$alkyl groups, $(C_1-C_6)$alkoxy groups, $A_1$ represents either —SH or —RaC=CRbRc and Ra, Rb and Rc represent independently a substituent chosen from the group consisting of a hydrogen atom and $(C_1-C_6)$alkyl groups.

According to one particular embodiment, $A_1$ represents —RaC=CRbRc with Ra, Rb and Rc representing independently a substituent chosen from the group consisting of a hydrogen atom and $(C_1-C_6)$alkyl groups, and preferably Ra, Rb and Rc representing all a hydrogen atom.

According to another particular embodiment, R1, R2 and R3 are $(C_1-C_6)$alkoxy groups or halogen atoms.

Preferably, R1, R2 and R3 are halogen atoms, more preferably chlorine atoms.

According to another particular embodiment, Ra, Rb and Rc all are hydrogen atoms.

According to yet another particular embodiment, X is chosen from the group consisting of $(C_1-C_{18})$alkylene and a 1,m-phenylene group with m=2, 3 or 4.

According to one other specific embodiment, the first step consists in exposing the substrate surface to an anchoring molecule comprising a silane group and an alkene group, and in reacting thereafter the alkene group with a dithiol molecule, preferably with dithiothreitol, thus functionalizing the substrate surface with a thiol group as $A_1$.

Advantageously, the reaction of the anchoring molecule with the substrate surface in the first step is carried out under efficient conditions to promote the reaction.

This reaction of the anchoring molecule with the substrate surface may be carried out notably in a liquid medium containing the anchoring molecule, for example a $(C_1-C_{18})$ alkenyltrichlorosilane, in a solvent, for example chosen from chloroform, dichloromethane, dry toluene or bicyclohexyl, for example at a concentration of 0.005-5% (v/v), preferably of 0.01-1% (v/v) and most preferably of 0.05-0.5% (v/v).

The temperature during this reaction of the anchoring molecule with the substrate surface may be maintained in particular between 0 and 50° C., preferably between 10 and 40° C. and most preferably between 15 and 30° C.

This reaction of the anchoring molecule with the substrate surface may be notably conducted under inert atmosphere, preferably under Ar, and may in particular last from 30 seconds to 24 hours, preferably from 5 minutes to 12 hours and most preferably from 1 to 6 hours.

In the reaction of the anchoring molecule with the substrate surface according to the specific embodiment as described above, the silane group —SiR1R2R3 reacts with the surface metal oxide or hydroxyl groups, while the group $A_1$ remains intact.

As a result of the first step, the anchoring molecule is covalently attached to the surface through the coupling of the silane groups with the surface oxide and/or hydroxyl groups.

It should be noted that, although it is possible to use a mixture of different anchoring molecules, the group $A_1$ should be of the same type, i.e. either alkenyl or thiol group, so that no premature thiol-ene reaction is carried out during the first step.

In the same way, where other reactants and/or other additives are present in the liquid medium, preferably they may not contain or contain only in trace quantities of an alkenyl, thiol or disulphide group capable of reacting prematurely with the group $A_1$ and preferably they may not contain or contain only in trace quantities a group capable of reacting prematurely with the silane group. Trace quantities may be less than 0.01 equivalents, notably less than 0.005 equivalents, preferably less than 0.001 equivalents with respect to the alkenyl or thiol group $A_1$.

Advantageously, a dense layer, and in particular a SAM of anchoring molecules has been formed as a result of the first step.

Figure 1:
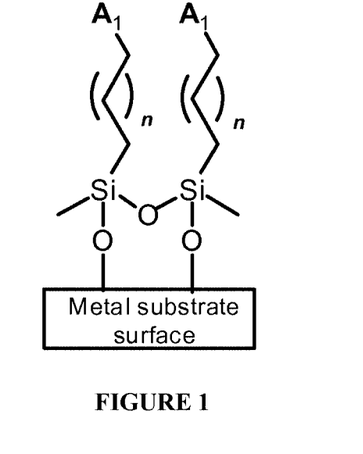
FIG. 1 represents schematically and not true to scale a layer of anchoring molecules covalently attached to a metallic substrate surface.

A layer of anchoring molecules bearing an $A_1$ group can be schematically represented as illustrated in FIG. 1.

Second Step: Grafting of Polymers

The second step of the method of modifying a substrate surface according to the present invention involves exposing the substrate surface with anchoring molecules covalently attached onto it to polymers carrying at least one group $A_2$ capable of reacting with the group $A_1$.

Polymers Carrying at Least One Group $A_2$

The polymer suitable for the method of the present invention is preferably a statistical polymer carrying on average from 3 to 600 $A_2$ groups per polymeric chain.

According to the present invention, the expression "a statistical polymer" means a polymer which carries at least three $A_2$ groups or reactive sites, randomly distributed on the polymeric chain.

The polymer suitable for the method of the present invention may carry one or more groups $A_2$, preferably at least three groups $A_2$, capable of reacting with the group $A_1$, $A_2$ being —SH or a group —S—S—R' when $A_1$ is an alkenyl group and $A_2$ being an alkenyl group when $A_1$ is —SH, with R' being a polymer or an oligomer.

In one particular embodiment, the group $A_2$ is
—SH or a group —S—S—R' when $A_1$ is an alkenyl group, or
an alkenyl group —RaC=CRbRc when $A_1$ is —SH, with Ra, Rb and Rc being any of the groups as defined above and with R' being a polymer or an oligomer, the repeating units of R' being identical to or different from the repeating units of the polymer carrying $A_2$. Where R' is a polymer with repeating units identical to those of the polymer carrying $A_2$, R' may be identical to or different from the polymer carrying $A_2$ with respect to the chain length and optional substitution.

In this particular embodiment, preferably the group $A_2$ is
—SH when $A_1$ is an alkenyl group, or
an alkenyl group —RaC=CRbRc when $A_1$ is —SH.

with Ra, Rb and Rc representing independently a substituent chosen from the group consisting of a hydrogen atom and $(C_1-C_6)$alkyl groups, and preferably Ra, Rb and Rc representing all a hydrogen atom.

In particular, when $A_1$ is —SH and $A_2$ is an alkenyl group —RaC=CRbRc, Ra, Rb and Rc may represent independently a substituent chosen from the group consisting of a hydrogen atom and $(C_1-C_6)$alkyl groups, and preferably Ra, Rb and Rc represent all a hydrogen atom.

In a preferred embodiment, the group $A_2$ is an alkenyl group —RaC=CRbRc and $A_1$ is —SH, with Ra, Rb and Rc representing independently a substituent chosen from the group consisting of a hydrogen atom and $(C_1-C_6)$alkyl groups, and preferably Ra, Rb and Rc representing all a hydrogen atom.

When $A_1$ is an alkenyl, $A_2$ is notably —SH or a group —S—S—R' with R' being a polymer or an oligomer, the repeating units of R' being identical to or different from the repeating units of the polymer carrying $A_2$, and preferably a polymer identical to the polymer carrying $A_2$.

Most preferably, $A_1$ is an alkenyl, notably —RaC=CRbRc as defined above, and $A_2$ is —SH.

In a preferred embodiment, the polymer carries at least one terminal group $A_2$ capable of reacting with the group $A_1$, and more preferably one terminal thiol group or one terminal group —S—S—R' with R' being as defined above, when $A_1$ is an alkenyl group.

The polymer may for example be chosen from the group consisting of polyethylenes, polyacrylamides, polyacrylates, polyvinyl polymers, polystyrenes, polyalcohols such as polyvinylalcohol and polyallylalcohol, polyvinylbenzyl polymers, polyamines such as polyethyleneimine and polyallylamin, polymethacrylates, polymethacrylamides, polyethers e.g. polyethylene glycol, polyesters e.g. poly(DL-lactide), polyamides, polyurethanes, poly(ethylene-alt-succinimide), polysaccharides such as dextran, cellulose, hydroxyethylcellulose and methylcellulose, polyureas, polyanilines, polypeptides, polypyrroles, polythiophenes, their mixtures, copolymers and derivatives.

If R' is a polymer, R' may be chosen from the same group as mentioned above for the polymer carrying at least one $A_2$, and if R' is an oligomer, the repeating units of the oligomer may be chosen from the repeating units constituting one of the polymers of said group.

In one embodiment, the polymer, which is preferably a statistical polymer, carrying at least one group $A_2$ has a number average molecular weight greater than 2 000 g/mol, preferably greater than 3 000 g/mol and more preferably greater than 5 000 g/mol. Preferably, said number average molecular weight may vary between 2 000 and 5 000 000 g/mol depending on the nature of the polymer, more preferably between 3 000 and 2 000 000 g/mol, in particular between 3 000 and 100 000 g/mol and for example between 5 000 and 10 000 g/mol.

The polymer may notably be a polyether, especially a polyethylene glycol, or a polysaccharide, especially a methylcellulose, for example having a number average molecular weight varying between 10 000 and 2 000 000 g/mol and preferably between 20 000 and 150 000 g/mol.

According to one particular embodiment, the polymer is a polyethylene glycol.

According to this particular embodiment, the polymer is a polyethylene glycol and has a number average molecular weight varying between 2 000 and 10 000 g/mol, and for example between 3 000 and 8 000 g/mol when $A_2$ is —SH or an alkenyl group. When $A_2$ is —S—S—R' with R' being a homologous polymer, the polymer may be a polyethylene glycol and have a number average molecular weight varying between 4 000 and 20 000 g/mol, and for example between 6 000 and 16 000 g/mol.

According to another particular embodiment, the polymer is a methylcellulose.

According to this particular embodiment, the polymer is a methylcellulose and has a number average molecular weight varying between 2 000 and 5 000 000 g/mol, more preferably between 10 000 and 2 000 000 g/mol, in particular between 20 000 and 150 000 g/mol and for example between 30 000 and 100 000 g/mol when $A_2$ is —SH or an alkenyl group. When $A_2$ is —S—S—R' with R' being a homologous polymer, the polymer may be a methylcellulose and have a number average molecular weight varying between 4 000 and 10 000 000 g/mol, more preferably between 20 000 and 4 000 000 g/mol, in particular between 40 000 and 300 000 g/mol and for example between 60 000 and 200 000 g/mol.

The table as shown below explains the link between viscosity of methylcellulose and some molecular weights (from Technical Handbook, Methocel Cellulose Ethers, 2002, p. 18).

| Viscosity Grade 2%, 20° C., mPa · s | Intrinsic Viscosity (h), dL/g | Number Average Degree of Polymerization | Number Average Molecular Weight (Mn) |
| --- | --- | --- | --- |
| 40 | 2.0 | 110 | 20 000 |
| 4000 | 7.5 | 460 | 86 000 |
| 8000 | 9.3 | 580 | 110 000 |
| 19000 | 12.0 | 750 | 140 000 |
| 40000 | 15.0 | 950 | 180 000 |

Advantageously, the second step reaction is carried out under efficient conditions to promote the reaction.

The second step may be carried out notably by pipetting a liquid medium containing the polymer comprising a group $A_2$, for example a poly (ethylene glycol) or a methylcellulose, for example at a concentration of 10-90% (v/v), preferably of 20-80% (v/v) and most preferably of 40-60% (v/v), i.e. of from 0.01 to 90 mg/mL, preferably of from 0.1 to 50 mg/mL, and most preferably of from 0.1 to 10 mg/mL and a photoinitiator such as described hereinafter, for example at a concentration of 0.1-100 mM, preferably of 1-50 mM and most preferably of 5-20 mM, i.e. of from 0.01 to 50% by weight with respect to the total volume of the solution, preferably of from 0.05 to 10% by weight with respect to the total volume of the solution, and most preferably of from 0.05 to 1% by weight with respect to the total volume of the solution in a solvent, for example chosen from water, glycerol, ethylene glycol, dichloromethane, chloroform and dimethylformamide. The substrate with the liquid medium pipetted on top may thereafter be covered with a cover slide, for example made of quartz, to form an assembly.

In a particular embodiment, when the polymer is methylcellulose and the group A2 is an alkenyl group, the amount of polymer in the second step (ii) is from 0.1 to 10 mg/mL with respect to the total volume of the solution.

The temperature during the second step may be maintained in particular between 0 and 50° C., preferably between 10 and 40° C. and most preferably between 15 and 30° C.

The second step may notably be photoactivated, i.e. it may be conducted by exposing the above mentioned assembly to UV light, for example at 0.5-20 mW/cm$^2$ (for example at 7.2 mW/cm$^2$, i.e. λ=254 nm), preferably 2-15 mW/cm$^2$ (for example at 5.2 mW/cm$^2$, i.e. λ=365 nm), and most preferably 4-8 mW/cm$^2$, notably at a wavelength adapted to the photoinitiator used, for in particular from 1 s to 24 h, preferably from 1 s to 1 h and most preferably from 10 s to 300 min.

Where other additives are present in the liquid medium, preferably they may not contain or contain only in trace quantities of an alkenyl, thiol, or disulphide group capable of detracting either group $A_1$ or $A_2$ from their intended reaction. Trace quantities may be less than 0.01 equivalents, notably less than 0.005 equivalents, preferably less than 0.001 equivalents with respect to the alkenyl or thiol group $A_1$.

According to one specific embodiment, the second step may be photo-initiated, notably by a photo-initiator appropriate for the second reaction step, as may be determined by a man skilled in the art. The photo-initiator is notably chosen from the group of initiators commercialized under the trade names IRGACURE or DAROCURE by the company BASF, and may for example be chosen from the group consisting of 1-Hydroxy-cyclohexyl-phenyl-ketone; 2-Hydroxy-2-methyl-1-phenyl-1-propanone; 2-Hydroxy-1-[4-(2-hydroxyethoxy)phenyl]-2-methyl-1-propanone; Methylbenzoylformate; oxy-phenyl-acetic acid 2-[2 oxo-2 phenyl-acetoxy-ethoxy]-ethyl ester; oxy-phenyl-acetic 2-[2-hydroxy-ethoxy]-ethyl ester; Alpha, alpha-dimethoxyalpha-phenylacetophenone; 2-Benzyl-2-(dimethylamino)-1-[4-(4-morpholinyl)phenyl]-1-butanone; 2-Methyl-1-[4-(methylthio)phenyl]-2-(4-morpholinyl)-1-propanone; Diphenyl (2,4,6-trimethylbenzoyl) phosphine oxide and phenyl bis (2,4,6-trimethyl benzoyl) phosphine oxide.

According to this specific embodiment, preferably the second step (ii) is carried out in the presence of a photoinitiator in a content of at most 10% by weight/vol, i.e. at most 10% by weight with respect to the total volume of the solution, preferably at most 5% by weight/vol, i.e. at most 5% by weight with respect to the total volume of the solution, and more preferably of at most 1% by weight/vol, i.e. at most 1% by weight with respect to the total volume of the solution.

Advantageously, the photo-initiator is 2,2-Dimethoxy-2-phenylacetophenone or 2-Benzyl-2-(dimethylamino)-1-[4-(4-morpholinyl)phenyl]-1-butanone.

According to another specific embodiment, the second step (ii) is carried out in the absence of a photoinitiator. The absence of a photoinitiator may be advantageous in terms of toxicity.

In this particular embodiment, the reaction may be carried out with a photoactivation, for example, at $\lambda=254$ nm or 365 nm, with or without the presence of a photoinitiator.

In a further particular embodiment, said step is carried out with a photoactivation, for example at $\lambda=254$ nm or 365 nm, in the presence of a photoinitiator in a content of 0 to 1% by weight/vol, i.e. of 0 to 1% by weight with respect to the total volume of the solution.

In this second step, the group $A_2$ of the polymer reacts with the freestanding group $A_1$ of the layer of anchoring molecules.

The reaction can be described by the following reaction scheme:

According to one particular embodiment, the polymer carrying at least one group $A_2$ may further carry at least one biomolecule as defined above such as peptides and proteins.

According to another particular embodiment, the method of modifying a substrate surface according to the present invention may further include pre-treatment steps, such as cleaning processes, other intermediate steps, such as a treatment/modification of the layer of anchoring molecules or a further substrate surface treatment, or post-treatment steps, such as work-up procedures. In particular, silicate and silicium substrates may be pre-treated by dispersing them in an aqueous $H_2O_2/H_2SO_4$ solution and titanium-based substrates may be pre-treated by ozonolysis and/or UV treatment.

According to another particular embodiment, the method of modifying a substrate surface according to the present invention may be used to confer to metal substrate surfaces modified properties which may be chosen from the group consisting of hydrophilic character; improved hydrophobic character, cytotoxic properties such as antibiotic, bactericidal, viricidal and/or fungicidal properties; cell-adhesion property; improved biocompatibility such as protein repellency or adhesion property; electric conductivity property and reactivity property which renders said surface able to immobilize biomolecules.

These modified properties may be investigated by any method known to the man skilled in the art and include notably contact angle measurements for hydrophilic/hydrophobic character and bacterial adhesion experiments combined with microscopic investigation for improved biocompatibility.

According to one preferred aspect of the present invention, this method is used to confer anti-adhesive properties to titanium-based materials.

i) R' = homologous polymer

As a result of the second step, the polymer is covalently attached to the surface via a thioether link to the layer of anchoring molecules, formed by the thiol-ene type reaction.

Thus, in a preferred embodiment, the anchoring molecule is covalently attached to the substrate surface as a result of the first step and the polymer is covalently attached to the anchoring molecule as a result of the second step.

Advantageously, a dense polymer monolayer has been formed as a result of the second step.

Figure 2:
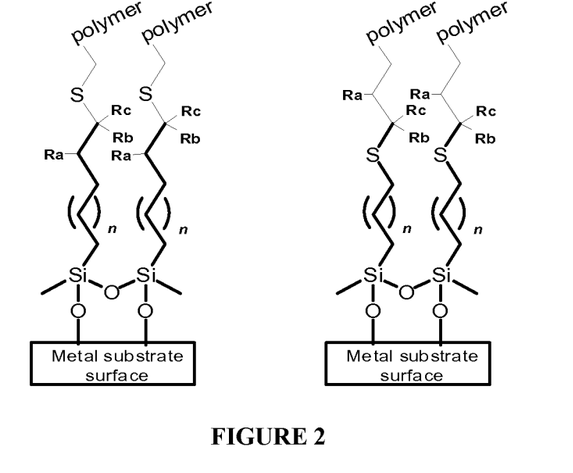
FIG. 2 represents schematically and not true to scale a polymer layer covalently attached to a layer of anchoring molecules on a metallic substrate surface.

The polymer layer can be schematically represented as illustrated in FIG. 2.

According to yet another particular embodiment, the method of modifying a substrate surface according to the present invention may be used to confer to the surface an immobilisation pattern, notably by employing a photo-filter during the photo-initiation of the second step.

This immobilisation pattern may lead to a pattern of different modified physical and/or biochemical properties conferred to the surface.

Applications

The method according to the present invention may be used in a variety of applications such as medical and/or research applications.

In one embodiment, the method of modifying a substrate surface as described above may confer an anti-adhesive property to medical implants, e.g. cardiovascular devices such as pacemaker cases, carrier structure for replacement of heart valves and intra-vascular stents, and to surgical instruments, notably to titanium-based implants and instruments.

In another particular embodiment, the method of modifying a substrate surface as described above may confer an adhesive and/or cell-growth promoting property to medical implants e.g. dental implants, bone and joint replacements such as prostheses of hips and knees or for internal/external bone-fracture fixation such as spinal fusion devices, pins, bone-plates, screws, intramedullary nails and external fixators, and implants used in maxillofacial and craniofacial treatments.

According to another specific embodiment, the method as described above is used for modifying the surface of a substrate which may be chosen from the group consisting of medical implants, such as dental implants, bone and joint replacements, implantable catheters with access port, stent and research tools such as chips and microarrays.

According to another aspect, the present invention relates also to metallic substrates, the surface of which has been treated by the method as described above.

In one particular embodiment, the metallic substrate is covalently grafted with a first layer, in particular a SAM of anchoring molecules and a second monolayer of polymers, attached to the layer of anchoring molecules via a thioether group.

Preferably, said metallic substrate with grafted layers as described above may be chosen from the group consisting of medical implants, such as dental implants, bone and joint replacements, implantable catheters with access port, stent and research tools such as chips and microarrays.

Depending on the size of the anchoring molecule and on the mass of the polymer, the thickness of the immobilised layers can range between 1 and a few tens of nanometers as illustrated in the examples. The thickness can advantageously be measured by ellipsometry. The resulting layer is a thin polymeric gel that is very robust against solvents and mechanical friction.

DESCRIPTION OF FIGURES

The figures are intended for purposes of illustrating and are not meant to be limiting the scope of the present invention.

The following examples illustrate the present invention without limiting its scope.

EXAMPLES

Materials

Solvents were purchased from SDS (Peypin, France).
Titanium substrates were purchased from Goodfellow (Lille, France).
Silicon (100) wafers covered by a native oxide layer were purchased from Neyco (Paris, France).
MeO-PEG-SH (Mw=5000 g/mol) was purchased from Rapp polymere (Tübingen, Germany).

Allyl-modified methylcellulose was prepared according to Example 7 (copolymer 11) as described in WO 2008/041187.

10-Undecenyltrichlorosilane was purchased from ABCR (Karlsruhe, Germany).

2,2-Dimethoxy-2-phenylacetophenone (IRGACURE 651) and 2-Benzyl-2-(dimethylamino)-4'-morpho linobutyrophenone (IRGACURE 369), O-(2-Mercaptoethyl)-O'-methyl-hexa(ethylene glycol) as well as FITC labelled BSA and fibrinogen were purchased from Sigma-Aldrich (Lyon, France).

A. Surface Modification of Metal Substrates

Ex. 1: Vinyl-Comprising Anchoring Molecules/PEG-SH on Ti Substrate 1.1 Preparation of Substrate for Monolayer Coating The titanium plates to be used as substrate were subjected to deep UV treatment using a UV grid lamp from UVP (Cambridge, UK), providing 20 mW/cm$^2$ ($\lambda$=185 nm), at room temperature during 10 min.

1.2 Deposition of the Vinyl-Comprising Anchoring Molecules

The substrate plates prepared according to step 1.1 were exposed to a monolayer deposition solution prepared by mixing 100 µL of 10-Undecenyltrichlorosilane with 100 mL of dry toluene solvent. The coating procedure was performed in Ar for 120 min at room temperature. Samples were withdrawn from the silane solutions and washed several times with $CHCl_3$, ethanol and then dried under nitrogen stream.

1.3 Grafting with a Thiol-Group Comprising Oligo(Ethylene Glycol)

Comparative

A mixture of 10 µL 2,2-Dimethoxy-2-phenylacetophenone (20 mM in ethylene glycol) and 10 µL of O-(2-Mercaptoethyl)-O'-methyl-hexa(ethylene glycol) was pipetted onto the substrate obtained in step 1.2 and covered with a quartz cover slide. The assembly was exposed to UV light for 10 seconds at room temperature, using a BIO-LINK BLX (Vilber Lourmat, France), providing 7.2 mW/cm$^2$ ($\lambda$=254 nm) at the surface. The slide was removed from the substrate and rinsed several times with ethanol and water.

1.4 Grafting with a Thiol-Group Comprising Poly(Ethylene Glycol)

Invention 5 mg of MeO-PEG-SH (Mw=5000 g/mol) were solubilized in 1 mL of a saturated water solution of photoinitiator 2-hydroxy-1-[4-(hydroxyethoxy)phenyl]-2-methyl-1-propanone (Irgacure-2959, Ciba-Geigy, 0.1 wt-% in water), pipetted onto the substrate obtained in step 1.2 and covered with a quartz cover slide. The assembly was exposed to UV light, for 1 minute at room temperature, using a CL-1000L crosslinker (UVP, USA), providing 5.2 mW/cm$^2$ ($\lambda$=365 nm), at the surface. The slide was removed from the substrate and rinsed several times with ethanol and water.

Ex. 2: Vinyl-Comprising Anchoring Molecules/PEG-SH on Si Substrate

2.1 Preparation of Substrate for Monolayer Coating

The silicon substrates were cleaned in chloroform, acetone, and ethanol, then blown dry in a filtered nitrogen stream and cleaned by immersion in a piranha solution ($H_2SO_4/H_2O_2$, 70:30 v/v, 80° C.) for 20 min and via ozonolysis to remove organic contaminants. This treatment was followed by three rinsings with deionized water and by drying under a filtered nitrogen stream.

2.2 Deposition of the Vinyl-Comprising Anchoring Molecules

The substrate plates prepared according to step 2.1 were exposed to a monolayer deposition solution prepared by mixing 100 µL of 10-Undecenyltrichlorosilane with 100 mL of dry toluene solvent. The coating procedure was performed in Ar for 120 min at room temperature. Samples were withdrawn from the silane solutions and washed several times with $CHCl_3$, ethanol and then dried under nitrogen stream.

2.3 Grafting with a Thiol-Group Comprising Poly(Ethylene Glycol)

Invention 5 mg of MeO-PEG-SH (Mw=5000 g/mol) were solubilized in 1 mL of a saturated water solution of photoinitiator 2-hydroxy-1-[4-(hydroxyethoxy)phenyl]-2-methyl-1-propanone (Irgacure-2959, Ciba-Geigy, 0.1 wt-% in water), pipetted onto the substrate obtained in step 2.2 and covered with a quartz cover slide. The assembly was exposed to UV light, for 1 minute at room temperature, using a CL-1000L crosslinker (UVP, USA), providing 5.2 mW/cm$^2$ ($\lambda$=365 nm), at the surface. The slide was removed from the substrate and rinsed several times with ethanol and water.

Ex. 3: Thiol-Comprising Anchoring Molecules/Allyl-Modified Methylcellulose on Si Substrate

3.1 Preparation of Substrate for Monolayer Coating

The silicon substrates were modified according to the procedure described under 2.1.

3.2 Deposition of the Anchoring Molecules and Functionalization with a Thiol Group 10-Undecenyltrichlorosilane was deposited according to the procedure described under 2.2. Then the alkene terminated surface is reacted with a solution of dithiothreitol (20 mM) and 2,2-Dimethoxy-2-phenylacetophenone (20 mM) in DMF during 10 min at room temperature using a BIO-LINK BLX (Vilber Lourmat, France), providing 7.2 mW/cm$^2$ ($\lambda$=254 nm) at the surface.

3.3 Grafting with an Allyl-Modified Methylcellulose 1 mg of allyl-modified methylcellulose were solubilized in 1 mL of a saturated water solution of photoinitiator 2-hydroxy-1-[4-(hydroxyethoxy)phenyl]-2-methyl-1-propanone (Irgacure-2959, Ciba-Geigy, 0.1 wt-% in water), pipetted onto the substrate obtained in step 3.2 and covered with a quartz cover slide. The assembly was exposed to UV light, for 1 hour at room temperature, using a CL-1000L crosslinker (UVP, USA), providing 5.2 mW/cm$^2$ ($\lambda$=365 nm), at the surface. The slide was removed from the substrate and rinsed several times with ethanol and water.

Ex. 4: Thiol-Comprising Anchoring Molecules/Allyl-Modified Methylcellulose on Ti Substrate

4.1: Preparation of Substrate for Monolayer Coating and Deposition of the Anchoring Molecules and Functionalization with a Thiol Group After cleaning, surfaces (titanium oxide $TiO_2$) were treated with a mercaptosilane: (3-mercaptopropyl)trimethoxysilane (MPTS) according the protocol published in *Langmuir*, 18 (2002) 846-854.

4.2: Preparation of Allyl-Modified Methylcellulose

In a round flask (250 mL) is dissolved, part by part, methylcellulose (1.5 g; 8.67.10-3 mol of units) in a cold solution of aqueous NaOH (400 mg in 200 mL of water at 0° C.). After complete dissolution (transparent, viscous, and slightly foamy solution) allylbromide (4 mL; 5 eq./unit) is added. The solution becomes milky white and is vigorously stirred at room temperature for 24 h. The polymer is then flocculated by rotating the solution in a warm bath (50-60° C.), several times until all polymer is aggregated (in a spongy gel). This gel is removed from the solution by filtration and dialyzed 2 days in water baths (3 L) for removal of reactants in excess (dialysis tube have to be rehydrated in water for 15 min before use). The polymer solution is then dried in an oven or lyophilized to obtain modified methycellulose as either a transparent film or a white porous material. Yield 60-70%. $^1$H-NMR (300 MHz, $D_2O$): δ 5.80 (m, 1H), 5.30 (m, 2H), 2.9-4.5 (m, 227H); ATR-FTIR (diamond): 3450 cm−1, 2830-3000 cm−1, 1615 cm−1, 1054 cm−1, 1300-1500 cm−1.

4.3: Grafting with a Vinyl-Modified Methylcellulose

The silanized titanium surface is incubated in an aqueous solution of methylcellulose bearing vinyl groups (1 mg/mL) and a photoinitiator (Irgacure 2939 (2-Hydroxy-4'-(2-hydroxyethoxy)-2-methylpropiophenone)), 0.1% w/v) under light exposure ($\lambda$=254 or 365 nm, 7.2 mW/cm2 or 5.2 mW/cm2) during 60 min. Then the surface is washed several times in water, ethanol.

B. Investigation of Modified Surface Properties

B.1. Bacterial Adhesion

The titanium substrates obtained in example 1 (steps 1.3, 1.4 and 4.3), as well as an unmodified titanium substrate were immersed in 20 mL of LB medium containing 100 µL of a bacterial innoculum (GFP labeled *E. coli* MG1655). The bacteria were allowed to grow overnight at 37° C. Then incubated substrates were washed with phosphate buffered saline in order to remove non adhesive bacteria.

B.2. Optical Microscopy

The substrates obtained in the preceding bacterial adhesion experiment were examined by optical microscopy using a Leica DMRX upright optical microscope. The images were recorded with a Retiga EXi CCD camera (QImaging, USA) and the bacteria counted on the image.

B.3. Contact Angle Measurements

The silicon substrates obtained in example 2 (steps 2.2 and 2.3) and in example 3 (step 3.3) were measured with a CA goniometer (Digidrop, GBX). The CAs were determined using water at room temperature (25° C.). For dynamic (advancing ($\theta_A$) and receding ($\theta_R$) CA measurement, water droplets (about 4 µL) were added and withdrawn from the surface, respectively. Measurements were taken at three different locations on each sample surface. The CA data reported was determined by averaging the averaged values of three samples (n=3) which were prepared in independent experiments.

B.4. Results

The results of the bacterial adhesion experiment for example 1 are summarised in table 1 and show that an anti-adhesive property has been conferred to the substrate surface by the method according to the invention.

TABLE 1

| | Bacterial density (*E. coli* MG1655, bacteria/cm$^2$) |
|---|---|
| Control (unmodified Ti substrate) | $1.9 \times 10^5$ |
| Oligo(ethylene glycol)-modified Ti substrate (step 1.3, comparative) | $1.6 \times 10^4$ |
| Poly(ethylene glycol)-modified Ti substrate (step 1.4, invention) | $1.9 \times 10^3$ |

The results of the bacterial adhesion experiment for example 4 are summarised in table 2 and show that an anti-adhesive property has been conferred to the substrate surface by the method according to the invention.

TABLE 2

| | Bacterial density (*E. coli* MG1655, bacteria/cm$^2$) |
|---|---|
| Control (unmodified Ti substrate) | 9637 |
| Ti modified with MPTS | 11523 |
| Methylcellulose-modified Ti substrate (step 4.3, invention) | 75 |

The results of the contact angle measurements are summarized in tables 3 and 4 and show that a hydrophilic property has been conferred to the substrate surfaces by the method according to the invention.

TABLE 3

| | Water contact angles (°) | |
|---|---|---|
| | advancing | receding |
| Alkene-modified Si substrate (step 2.2, intermediate SAM of invention) | 101 | 94 |
| Poly(ethylene glycol)-modified Si substrate (step 2.3, invention) | 54 | 18 |

TABLE 4

| | Water contact angles (°) | |
|---|---|---|
| | advancing | receding |
| Methylcellulose-modified Si substrate (step 3.3, invention) | 58 | 12 |

The invention claimed is:

1. A method of conferring modified properties to a metallic substrate surface, the surface being formed at least partly by metal oxides, comprising:
   (i) a first step comprising at least exposing said substrate surface to a hetero-bifunctional anchoring molecule carrying at least a silane group and at least a $A_1$ group, said $A_1$ group being optionally introduced within said anchoring molecule via a preliminary functionalizing step, and
   (ii) a second step of exposing the substrate surface to a polymer carrying at least three groups $A_2$ capable of reacting with $A_1$, the second step being carried out after the first step,
   the group $A_1$ being an alkenyl group or —SH and the group $A_2$ being —SH or a group —S—S—R' when $A_1$ is an alkenyl group and $A_2$ being an alkenyl group when $A_1$ is —SH, with R' being a polymer,
   wherein said polymer has a number average molecular weight between 2,000 and 5,000,000 g/mol.

2. Method according to claim 1, wherein the anchoring molecule is covalently attached to the substrate surface as a result of the first step and wherein the polymer is covalently attached to the anchoring molecule as a result of the second step.

3. Method according to claim 1, wherein the modified properties conferred to the metal substrate surface are chosen from the group consisting of hydrophilic character; improved hydrophobic character; cytotoxic properties; antibiotic, bactericidal, viricidal and/or fungicidal properties; cell-adhesion property; improved biocompatibility; protein repellency; adhesion property; electric conductivity property and reactivity property rendering said surface able to immobilize biomolecules.

4. Method according to claim 1, wherein said polymer is chosen from the group consisting of polyethylenes, polyacrylamides, polyacrylates, polyvinyl polymers, polystyrenes, polyalcohols, polyvinylalcohols, polyallylalcohols, polyvinylbenzyl polymers, polyamines, polyethyleneimines, polyallylamines, polymethacrylates, polymethacrylamides, polyethers, polyethylene glycols, polyesters, poly(DL-lactides), polyamides, polyurethanes, poly(ethylene-alt-succinimides), polysaccharides, dextrans, celluloses, hydroxyethylcelluloses, methylcelluloses, polyureas, polyanilines, polypeptides, polypyrroles and polythiophenes, their mixtures, copolymers and derivatives.

5. Method according to claim 1, wherein said polymer is a polyether or a polysaccharide.

6. Method according to claim 1, wherein the anchoring molecule is of the following formula (I):

wherein:

X represents a bivalent group chosen from the group consisting of a $(C_1-C_{18})$alkylene group optionally interrupted by 1 to 3 $(C_1-C_4)$alkenylene groups and/or 1 to 3 $(C_5-C_{10})$arylene groups and/or optionally substituted by 1 to 3 $(C_1-C_4)$alkenyl groups and/or 1 to 3 $(C_5-C_{10})$ aryl groups, a bifunctional statistical polymer having a molecular mass of about 1,000 to 10,000 g/mol, and a 1,m-phenylene group with m=2, 3 or 4, R1, R2 and R3 represent independently a substituent chosen from the group consisting of a hydrogen atom, halogen atoms, $(C_1-C_6)$alkyl groups, $(C_1-C_6)$alkoxy groups, $A_1$ represents either —SH or —RaC=CRbRc and Ra, Rb and Rc represent independently a substituent chosen from the group consisting of a hydrogen atom and $(C_1-C_6)$alkyl groups.

7. Method according to claim 1, wherein the group $A_2$ is an alkenyl group —RaC=CRbRc and $A_1$ is —SH, with Ra, Rb and Rc representing independently a substituent chosen from the group consisting of a hydrogen atom and $(C_1-C_6)$ alkyl groups.

8. Method according to claim 1, wherein the substrate is a titanium-based material, a silicon-based material comprising a silicium oxide surface, or an iron-based material comprising an iron oxide surface.

9. Method according to claim 1, wherein the second step (ii) is carried out in the presence of a photoinitator in a content of at most 10% by weight with respect to the total volume of the solution.

10. Method according to claim 1, wherein the second step (ii) is carried out with photoactivation, in the presence of a photoinitator in a content of 0 to 1% by weight with respect to the total volume of the solution.

11. Method according to claim 1, wherein the substrate is chosen from the group consisting of medical implants and research tools.

12. Method according to claim 1, wherein the method confers an anti-adhesive property to medical implants and to surgical instruments, or confers an adhesive and/or cell-growth promoting property to medical implants or for internal/external bone-fracture fixation, and implants used in maxillofacial and craniofacial treatments.

13. A method of conferring modified properties to a metallic substrate surface, the surface being formed at least partly by metal oxides, comprising:

(i) a first step comprising at least exposing said substrate surface to a hetero-bifunctional anchoring molecule carrying at least a silane group and at least a $A_1$ group, said $A_1$ group being optionally introduced within said anchoring molecule via a preliminary functionalizing step, and (ii) a second step of exposing the substrate surface to a polymer carrying at least one group $A_2$ capable of reacting with $A_1$, the second step being carried out after the first step, the group $A_1$ being an alkenyl group and the group $A_2$ being —SH or a group —S—S—R' with R' being a polymer, the number average molecular weight of said polymer being greater than 1,000 g/mol.

* * * * *